United States Patent [19]
Dyckman et al.

[11] Patent Number: 6,034,282
[45] Date of Patent: *Mar. 7, 2000

[54] METHOD OF PHENOL TAR DESALTING

[75] Inventors: Arkady S. Dyckman; Vladimir I. Sarge; Yelena N. Sarge; Boris I. Gorovits, all of St Petersburg, Russian Federation

[73] Assignee: General Electric Company, Schenectady, N.Y.

[ * ] Notice: This patent is subject to a terminal disclaimer.

[21] Appl. No.: 09/127,489

[22] Filed: Jul. 31, 1998

Related U.S. Application Data

[63] Continuation of application No. 08/869,384, Jun. 5, 1997, Pat. No. 5,847,235, which is a continuation of application No. 08/531,352, Sep. 20, 1995, abandoned.

[30] Foreign Application Priority Data

Nov. 23, 1994 [RU] Russian Federation ................ 940401

[51] Int. Cl.[7] ................................................ C07C 39/12
[52] U.S. Cl. .............................................. 568/754
[58] Field of Search ............................... 568/754

[56] References Cited

U.S. PATENT DOCUMENTS

| | | |
|---|---|---|
| 2,029,687 | 2/1936 | Wilson . |
| 3,979,281 | 9/1976 | Gerhold . |
| 4,016,213 | 4/1977 | Yeh et al. . |
| 4,173,587 | 11/1979 | Wu et al. . |
| 4,207,264 | 6/1980 | Anderson et al. . |
| 4,310,712 | 1/1982 | Langley . |
| 4,358,618 | 11/1982 | Sifniades et al. . |
| 4,548,711 | 10/1985 | Coombs . |
| 4,929,786 | 5/1990 | Himmele et al. . |
| 5,015,786 | 5/1991 | Araki et al. . |
| 5,017,729 | 5/1991 | Fukuhara et al. . |
| 5,144,094 | 9/1992 | Richmond et al. . |
| 5,254,751 | 10/1993 | Zakoshansky . |
| 5,283,376 | 2/1994 | Dyckman et al. . |
| 5,371,305 | 12/1994 | Hood . |
| 5,510,543 | 4/1996 | Fulmer . |

FOREIGN PATENT DOCUMENTS

| | | |
|---|---|---|
| 0 032 255 A1 | 12/1979 | European Pat. Off. . |
| 0 028 910 A1 | 11/1980 | European Pat. Off. . |
| 57080-332 | 11/1980 | Japan . |

OTHER PUBLICATIONS

Ind. Eng. Chem Res. 1988, 27, 4–7 "Side Reactions in the Phenol/Acetone Process. A Kinetic Study".

*Primary Examiner*—Michael L. Shippen

[57] ABSTRACT

A method for reduction of salt content in phenol tars with no additional solvent which washes the tars with water alone in a countercurrent flow extractor and substantially reduces the level of salt in the tar.

12 Claims, No Drawings

METHOD OF PHENOL TAR DESALTING

This application is a continuation of U.S. Ser. No. 08/869,384 filed Jun. 5, 1997, now U.S. Pat. No. 5,847,235, which is a continuation of U.S. Ser. No. 08/531,352 filed Sep. 20, 1995, now abandoned.

This invention relates generally to the process for manufacture of phenol from cumene. In this process, cumene is first oxidized to a cumene hydroperoxide intermediate which is then decomposed with an acid catalyst in a second step to form the crude mixture of phenol, acetone and by-products. Prior to distillation and products recovery, it is necessary to remove the catalyst acid via a neutralization process using base. The inorganic salts that are formed here and partially exit the process with the tars that are formed must be effectively removed to prevent fouling of downstream equipment and contamination of the phenol tar stream which is incinerated.

As environmental restrictions become more stringent, it is critical to lower the volume of unusable wastes generated by the process. One of the more promising avenues in minimize wastes is to recover more useful products from the tar streams. However, the presence of salts in the tars interferes with these recovery processes by causing equipment fouling and corrosion. As the residual tar volume decreases the salt concentration increases, thus, leading to corrosion problems in the incineration system. Thus, an efficient tar recovery and disposition system requires an innovative efficient approach to lessen the salt levels in these tars to facilitate product recovery from these tar streams and lessen the level of corrosion and fouling in disposal equipment.

The phenol tar stream is a complex material consisting of many components including phenol, acetophenone (AP), α,α-dimethyl benzylalcohol (DMBA), dimers of α-methelstyrene (DMS) o,p-cumylphenol (PCP), unidentified components, and small amount of salts (mainly $Na_2SO_4$) and α methylstyrene (AMS). The exact phenol tar composition is dependent on the specific phenol production technology and can vary over a wide range.

| Component | Weight percent |
| --- | --- |
| AP | 5–30 |
| PCP | 10–50 |
| Phenol | 5–40 |
| DMS | 3–35 |
| DMBA | 1–15 |
| Residue | 1–65 |
| Salts | 0–2 |
| AMS | less than 0.1 |

Because of the presence of salts and the variation in composition, phenol tar has not found uses of substantial commercial value and is primarily used as fuel oil or incinerated as waste of no value. However, even when incinerated, the presence of both salts and phenol in the tar causes unacceptable air pollution by the phenolic compounds and particulates produced in incineration and corrosion and scale build up in the burners because of the salt content.

To date phenol tar processing has been aimed at phenol recovery since phenol is present in the tar in a relatively large quantity and has substantial value. In these processes, removal of salt is either not attempted or requires a completely separate process as set forth in U.S. Pat. No. 5,283,376.

One method disclosed for phenol tar desalting processed the tar at a temperature of from 50–60° C. with sulfuric acid mixed with the tar in an amount to provide 10% acid by weight based on the total quantity of phenol tar. The resultant reaction mass was washed with water, allowed to settle and the phenol tar was separated from the salt solution by decanting. Unfortunately this method substantially increases the level of waste water generated causing a greater deleterious impact on the environment.

Another method uses ammonia to extract phenol from the phenol tar. A 2 to 5% by weight ammonia solution in water at ambient temperature is mixed with phenol tar at a weight ratio of from 1 to 1.5 to 1 to 4, allowed to settle and then separated into organic and water phases. The level of salt removal depends on the effectiveness of the extracting agent. Other shortcomings of this process are:

1. Large volume and cost of the extracting agent increases the cost of the process and requires large volume equipment to accommodate the high volume of extracting agent.

2. Phenol tar must be cooled to about 25° C. before entering the extraction process to avoid excessive loss of ammonia through evaporation. This increases tar viscosity making the tar more difficult to handle.

As can be seen, each of the prior art processes for tar desalting have the common disadvantage of employing a water borne extracting agent which requires periodic regeneration. Regeneration increases costs and requires additional investment in equipment for regeneration of the extracting agent.

In order to overcome these disadvantages, the present invention:

provides an equivalent level of desalting efficiency with a substantial reduction in extracting agent usage expands the temperature range of the desalting process desalts the phenol tar with water alone as extractant, without the addition of any chemicals does not form emulsions which then must be broken The method of the present invention comprises contacting at a temperature of from about 10° C. to about 90° C. phenol tar containing salt with water at a feed ratio by weight of phenol tar to water of at least 1 to 0.3 in a multi-stage counter current flow extractor unit whereby the tar and water are admixed. The salt is removed in the water effluent. Because no additives are required in order to extract the salts from the tar, the water and tar phases rapidly separate after admixture efficiently removing substantially all of the salts from the tar. Since neither water in organic or organic in water stable emulsions are formed, no additives are needed to break the emulsions as necessary in the processes of the prior art. The efficiency of a counter current water wash was not heretofore recognized by skilled artisans because the prior art processes failed to provide the high degree of phase separation of the tar and water streams afforded by the counterflow of the present process.

For maximum extraction efficiency the water passes through the extraction vessel only once and then is disposed of in an ecologically effective manner. In water shortage areas, the water can be recirculated to the countercurrent extractor up to as many as 5 times, preferably 3 times and more preferably 2 times and still maintain acceptable extraction efficiency. It is more economic to recirculate the water than to raise the phenol tar to water feed ratio above 0.3 to 1. However, in times of extreme water shortage the extraction process will reduce salt levels somewhat when the ratio is as high as 0.5.

With respect to the temperature of the extraction process it is operated from about 10° C. to about 90° C., preferably from about 15° C. to about 80° C. and more preferably from about 20° C. to about 70° C. In the present process, the salt range in the phenol tar is reduced from 0.11–1.10% by about 20% by weight, preferably 90% and more preferably 99%. The key to the extraction process is the intimate admixture of the phenol tar and the water followed by efficient phase separation. No extra solvents are employed to dilute the phenol tar to make it less viscous in order to facilitate intimate admixture and then efficient phase separation.

Surprisingly the direct contact of undiluted phenol tar with water alone in the present process gives superior extraction performance. Admixture of phenol tar alone with water alone is usually sufficient as a result of the turbulence from the countercurrent flows in the reactor. Intimate admixture may be enhanced by installing in the extractor any of the state of the art mixing devices such as strategically located baffles which act as static mixers, paddles, anchor stirrers reciprocating trays, pulsing column extractor or any like devices of the prior art which increase turbulence in the extractor. In a multi-stage pulsing column, a reciprocating pump "pulses" the entire contents of the column at frequent intervals, so that a rapid reciprocating motion of relatively small amplitude is super-imposed on the usual flow of the liquid phases. The multi-stage tower may contain ordinary packing of special sieve plates. In a packed tower the pulsation disperses the liquids and eliminates channeling, and the contact between the phases is greatly improved. In sieve-plate pulse towers the holes are smaller than in non-pulsing towers, ranging from 1.5 to 3 mm in diameter, with a total open area in each plate of 6 to 23 percent of the cross-sectional area of the tower. Such towers are used almost entirely for processing highly corrosive reactive liquids. No downcomers are used. Ideally the pulsation causes light liquid to be dispersed into the heavy phase on the upward stroke and the heavy phase to jet into the light phase on the downward stroke. Under these conditions the stage efficiency may reach 70 percent. This is possible, however, only when the volumes of the two phases are nearly the same and where there is almost no volume change during extraction. In the more usual case the successive dispersions are less effective, and there is backmixing of one phase in one direction. The plate efficiency then drops to about 30 percent. Nevertheless, in both packed and sieve-plate pulse columns the height required for a given number of theoretical contacts is often less than one-third that required in an unpulsed column.

To provide intensive mass transfer in a pulsing extractor, liquids in contact are in oscillating (push-pull) motion of defined amplitude and frequency. Thus, vibration motion frequently is transformed into other types of motion in the contact units (e.g. into rotating movement). This leads to more even distribution or dispersion of one phase in to the other and increases the contact surface between the phases. Moving in continuous phase, dispersed particles combine or coalesce forming larger drops which split and return to the contact units. So, pulsation provides multiple surface interactions and increases the surface area by reduction of average drop dimension. All this increases the mass transfer index.

In the hydrodynamic mode of a pulsing column equipped with contact units (trays), operation is determined by the physical and chemical properties of the phases in contact (surface tension, viscosity, difference in densities, etc.) and pulsation intensity. Pulsation intensity J ordinarily is characterized as twice the amplitude multiplied by the pulsation frequency.

To perform salt extraction from phenol tar using water, a countercurrent column-type multi-stage pulsing extractor is preferable. Extractant (water) feeds into the bottom part of the column and fills it as a continuous phase. The extract output exits from the top of the column. Phenol tar (heavy phase) feeds into the top of column, goes through the column in a direction opposite to the flow of extract and is dispersed on the trays. Desalted tar collects in the bottom of the column and exits the reactor from the bottom. Phase pulsation is provided by an external pneumatic pulsator.

There are several hydrodynamic modes of the pulsing column operation dependent on pulsation intensity:

1. Insufficient pulsation intensity. One can observe column "choke", i.e. one of the phases locks into the other one, stopping it to from going through the column. There is no mass transfer in this mode.

2. Pulsation intensity is increased. Hydrodynamic of this mode corresponds to a discrete mixer—sedimentator mode. During the oscillation phase when the liquid goes down, phenol tar (heavy phase), which forms a layer on the tray, squeezes through the tray holes as large globules which drop onto next lower tray, where they coalesce. In the next oscillation phase, when the liquid goes up, the light phase (water) runs through the tar layer and phase inversion occurs. In every pulsation cycle, the heavy phase shifts down one tray. This mixing-sedimentating mode is not very effective because of the short contact time and small phase contact surface.

3. A further increase of pulsation intensity provides a split of drops and decreases the rate of their shifting from tray to tray. This mode provides a highly effective mass transfer. Ordinarily, industrial extractors are operated in this manner. Such a dispersion system can be characterized by an even distribution of similar size drops of the heavy phase which fill all of the between-tray volume. The contact surface in this case is several times more than it is in the second mode, and mass transfer index is of the highest value.

4. A higher pulsation intensity leads to unstable regime which can be characterized by a more tight drop pack and local coalescence (formation of unstable emulsion aggregates, leading to local "chokes").

5. A further rise of pulsation intensity leads to total "choking" of the extraction column.

The pulsing operation mode provides a well-dispersed heavy phase moving through the continuous light phase without emulsion formation and mechanical capture of either phase by the other for systems such as phenol tar—water, having a small density difference of about 0.05 g/cm$^3$). It is preferable to maintain phenol tar flow through the extractor to provide a residence time of the tar of at least 2, more preferable at least 5 and most preferable at least 10.

The actual equilibrium stages of phase contact are an indication of intimate admixture achieved. In the practice of the present invention, the actual equilibrium stages of phase contact are usually in the range of from about 1 to about 10, preferably from about 2 to 8, more preferably from about 3 to about 6 and most preferably from about 3 to about 4.

Whereas the prior art has focused on the need for chemicals to enhance extraction efficiency, the inventors hereof have determined that water alone is most effective with adequate admixture. Adequate admixture results when the pulsation intensity provides a splitting of the tar into droplets and decreases the rate of shifting of the tar droplets from tray to tray. This level of pulsation intensity is accomplished by gradually increasing the pulsation intensity until tar droplets are visible through lighted observation ports in the reactor. When adjusted to this level of pulsation intensity quite readily by the skilled artisan an even distribution of tar droplets of substantially the same size is formed and these droplets of tar dispersed in water substantially fill the entire volume between the trays, maximize the contact surface between the continuous water phase and the discontinuous tar phase and give a mass transfer index of the highest value.

Thus, the advantages of the present process are;

1. Usage of water alone as an extracting agent gives minimal reagent cost.
2. No dilution of phenol tar with solvent reduces environmental impact.
3. No additional solvents or chemicals needed for intimate admixture or efficient phase separation.
4. Broad temperature range gives highly flexible operation.
5. High degree of salt removal (over 95%).
6. Tar/water equilibrium is achieved almost immediately.

The advantages of the process suggested are confirmed by the following examples:

EXAMPLE 1

A phenol tar stream having a composition wt. % as follows: salts 0.139, phenol 17.2, AP 19.2, DMBA 11.8, DMS 10.6, AMS 0.08, CP 15.1 and unknowns 3.82, is processed by counter-current liquid extraction with water at 85° C. in a multi-stage pulsing column extractor.

The feed ratio of phenol tar to extracting agent (water) is 1:0.5. The extractor provides 6 theoretical equilibrium stages of phase contact. The water and tar streams rapidly separate after leaving the pulsing column extractor into two phases which are separated by decanting.

As a result of this extraction process a sufficient quantity of the salts is removed from the phenol tar so that the salt content remaining in the tar is 0.001% which corresponds to degree of salt removal equal to 99.2%.

EXAMPLE 2

Phenol tar (same composition as in Example 1) is processed by water in the pulsing column extractor providing 3 theoretical equilibrium stages of phase contact at 25° C. and feed ratio of tar to water is 1:1.5. The remaining salt content at extractor outlet was 0.003%, degree of salt removal was 97.8%.

EXAMPLE 3

Phenol tar stream of following composition, % by weight: salt 0.087, phenol 15.72, AP 17.52, DMBA 6.68, DMS 7.08, AMS 0.43, PCP 11.37, unknown components to 100%, is fed to the extractor as in Example 1 with water at a pulsation intensity J=44 mm/sec., a feed ratio of 1/1, temperature of 50° C. The extractor provides 3 theoretical stages of phase contact. Salt remaining in the phenol tar after exiting the extractor is 0.0015 weight % which corresponds to a degree of extraction of 98.3% by weight.

EXAMPLE 4

Phenol tar of the same composition as in Example 3 is fed into the extractor of Example 1, with water at a temperature of 50° C., pulsation intensity of 15 mm/sec., feed ratio of water/phenol tar of 0.75/1. The Extractor provides 1 theoretical stage of phase contact. Salt remainder in phenol tar after extractor is 0.053 weight % which corresponds to a degree of extraction of 36% by weight.

It should be understood that the examples are given for the purpose of illustration and do not limit the invention.

We claim:

1. A process for reducing the level of salt resulting from neutralization of catalyst acid in a phenol tar from a phenol-from cumene process, which comprises: admixing in an extractor the phenol tar, which comprises salt, at a temperature of from about 10° to about 90° C. with an extraction liquid consisting essentially of water, in a tar to extraction liquid feed ratio of at least 0.3/1, wherein the tar and extraction liquid do not form a stable emulsion and the level of salt is reduced by at least 20 percent by weight.

2. The process of claim 1 wherein the extractor has baffles which act as a static mixer to increase the intensity of admixture of the counter current flow.

3. The process of claim 1 wherein the extractor contains agitation means additionally to counter current flow.

4. The process of claim 3 wherein the agitation means is a rotating anchor stirrer.

5. The process of claim 3 wherein the agitation means is rotating paddles.

6. The process of claim 3 wherein the agitation means is reciprocating trays.

7. The process of claim 3 wherein the agitation means is a pulsing column extractor.

8. The process of claim 1 wherein the residence time of the tar in the extractor is at least ten minutes.

9. The process of claim 7 wherein the extractor provides at least one theoretical equilibrium stage of phase contact.

10. The process of claim 1 wherein the water is recirculated to the extractor at least once.

11. The process of claim 1 wherein the water is not recirculated to the extractor.

12. The process of claim 1 wherein the extractor is a packed column.

* * * * *